(12) United States Patent
Weber-Dabrowska et al.

(10) Patent No.: US 8,440,446 B2
(45) Date of Patent: May 14, 2013

(54) **BACTERIOPHAGE STRAINS FOR THE TREATMENT OF BACTERIAL INFECTIONS, ESPECIALLY DRUG RESISTANT STRAINS OF THE GENUS *ENTEROCOCCUS***

(75) Inventors: Beata Weber-Dabrowska, Wroclaw (PL); Andrzej Górski, Wroclaw (PL); Ryszard Miedzybrodzki, Wroclaw (PL)

(73) Assignee: Instytut Immunologii I Terapii Doswiadzalnej Pan, Wroclaw (PL)

( * ) Notice: Subject to any disclaimer, the term of this patent is extended or adjusted under 35 U.S.C. 154(b) by 0 days.

(21) Appl. No.: 13/059,513

(22) PCT Filed: Sep. 27, 2009

(86) PCT No.: PCT/PL2009/050025
§ 371 (c)(1),
(2), (4) Date: Jul. 13, 2011

(87) PCT Pub. No.: WO2010/036132
PCT Pub. Date: Apr. 1, 2010

(65) Prior Publication Data
US 2012/0122186 A1    May 17, 2012

(30) Foreign Application Priority Data
Sep. 29, 2008 (PL) .......................... 386175

(51) Int. Cl.
*C12N 7/00* (2006.01)
*A01N 63/00* (2006.01)
(52) U.S. Cl.
USPC ...................................... 435/235.1; 424/93.1

(58) Field of Classification Search ...................... None
See application file for complete search history.

(56) References Cited

PUBLICATIONS

WO 2000/69269 A1 (Exponential Biotherapies Inc. [US]; Nat Inst of Helth [US]; Merril Carl) Nov. 23, 2000.
International Search Report issued by the International Searching Authority (ISA/O.E.P.M.) on Dec. 23, 2009 in connection with International Application No. PCT/PL2009/050025.
Written Opinion of the International Searching Authority for PCT/IB2009/006939, dated Apr. 27, 2011.
International Preliminary Report on Patentability Chapter for PCT/IB2009/006939, dated May 3, 2011.
Indications Relating to Deposited Microorganism or Other Biological Material(s) or Other Biological Material (Form PCT/RO/134), dated Apr. 1, 2010.
Response to Communication Pursuant to Rules 161(1) and 162 EPC submitted to the European Patent Office in connection with European Patent Application No. 09 753 232.9-1223, dated Nov. 11, 2011.
Communication Pursuant to Article 94(3) EPC issued in connection with European Patent Application No. 09 753 232.9-1223, dated Jan. 12, 2012.
Response to Communication Pursuant to Article 94(3) EPC issued in connection with European Patent Application No. 09 753 232.9-1223, dated Apr. 20, 2012.

*Primary Examiner* — Zachariah Lucas
*Assistant Examiner* — Nicole Kinsey White
(74) *Attorney, Agent, or Firm* — Gary J. Gershik; Cooper & Dunham LLP

(57) ABSTRACT

Novel bacteriophage strains are disclosed and their use in the production of preparations for use in the treatment of bacterial infections, particularly with drug resistant strains of bacteria of the genus *Enterococcus*, particularly those belonging to the species *Enterococcus faecalis*.

10 Claims, No Drawings

BACTERIOPHAGE STRAINS FOR THE TREATMENT OF BACTERIAL INFECTIONS, ESPECIALLY DRUG RESISTANT STRAINS OF THE GENUS *ENTEROCOCCUS*

AREA OF THE INVENTION

The present invention relates to novel strains of bacteriophages and their use in the treatment of bacterial infections, particularly with strains of drug resistant bacteria of the genus *Enterococcus*.

PRIOR ART

Bacteriophages (phages) comprise a varied group of viruses, whose life cycle is connected exclusively to bacterial cells. Bacteriophages are characterised by a lytic or lysogenic life cycle. Lytic bacteriophages are most useful as antibacterial agents, which replicate in sensitive bacteria they infect, causing their complete destruction (lysis), and the new phages then attack and destroy subsequent bacterial cells. This process occurs both in vitro and in vivo.

One of the significant characteristics of bacteriophages is the commonly known specificity of their lytic activity. This characteristic is used, for example in the typing of bacteria (for examples see patent descriptions GB 2285684, U.S. Pat. No. 5,824,468, SU 543260, and international patent applications WO 0100786, WO 0109370). Other known uses of bacteriophages encompass: the use of bacteriophages as tools in molecular biology useful in the expression and selection of desirable proteins (i.e. patent description U.S. Pat. No. 6,027,930), use of phages in sterilising and cleaning products (i.e. patent description EP 0414304, EP 0290295, GB 2253859 as well as the international patent descriptions WO 9808944 and WO 9003122). Modified phages were used in the production of vaccines (i.e. WO 9505454). A number of proteins from bacteriophages are also used (i.e. EP 0510907, U.S. Pat. No. 5,470,573, WO 9607329). The methods of isolating bacteriophages and producing phage preparations are well known and continually improved (i.e. GB 829266, CS 192212, RU 2109055).

Phage therapy is was used as far back as WW II at the Institute of Microbiology and Virology in Tbilisi (Georgia). Pools of various phage preparations are used there in the treatment of bacterial infections and prophylaxis. Available data show the great effectiveness of phage therapy. Similar research has been performed in Poland, at the Bacteriophage Laboratory of the Institute of Immunology and Experimental Therapy in Wrocł aw, where phage therapy of infections with drug resistant and antibiotic-immune bacteria has been researched for 25 years (see: Stefan Ślopek et al., Archivum Immunologiae et Therapiae Experimentalis, 1981, 31, 293; Stefan Ślopek et al., Archivum Immunologiae et Therapiae Experimentalis, 1983, 31, 267; Stefan Ślopek et al., Archivum Immunologiae et Therapiae Experimentalis, 1984, 32, 317; Stefan Ślopek et al., Archivum Immunologiae et Therapiae Experimentalis, 1985, 33, 219; Stefan Ślopek et al., Archivum Immunologiae et Therapiae Experimentalis, 1985, 33, 241; Stefan Ślopek et al., Archivum Immunologiae et Therapiae Experimentalis, 1987, 35, 569; Beata Weber-Dą browska et al., Archivum Immunologiae et Therapiae Experimentalis, 2000, 48, 31-37; Beata Weber-Dą browska et al., Archivum Immunologiae et Therapiae Experimentalis, 2000, 48, 547-551).

Patent description P-370662 relates to multivalent bacteriophage strains, methods of producing them and use in the treatment of bacterial infections, particularly drug resistant strains of *Psedomonas* and *Staphylococcus*.

Particularly difficult problems are caused infections of the prostate and urinary tract caused by drug resistant bacteria, most often of the genus *Enterococcus*. Treatment of such infections with available antibiotics has caused worldwide therapeutic problems in recent years. The antibiotic therapy of these infections is becoming less and less effective since a prevalent majority bacterial strains exhibits resistance to all antibiotics, including the "last chance" antibiotic vancomycine. An acute need thus exists of introducing an alternative method of treating persistent and very dangerous bacterial infections.

Goal of the Present Invention

In recent years, there has been a massive rise in the distribution of bacterial strains resistant to all antibiotics, including the "last chance" antibiotic vancomycine. As a result, the antibiotic treatment of infections caused by drug resistant forms is ineffective.

This state of affairs causes great therapeutic problems. There is thus an acute need introducing an alternative method of treating persistent bacterial infections.

In light of the above, the goal of the present invention is to produce multivalent phage preparations, which could be used successfully to treat bacterial infections caused by drug resistant clinical strains of the *Enterococcus*, particularly those belonging to the species *Enterococcus faecalis*.

Unexpectedly, the goal stated above has been solved by the present invention.

The subject the present invention is bacteriophage strain specific against bacteria of the genus *Enterococcus* deposited in the Polish Microorganism Collection under as deposit number PCM F/00029.

The next subject of the present invention is the use of the bacteriophage strain deposited in the Polish Microorganism Collection as deposit number PCM F/00029 in the production of antibacterial preparations used to combat bacteria belonging to the genus *Enterococcus*. Preferentially, the targeted bacteria belong to the species *Enterococcus faecalis*.

Another subject the present invention is a bacteriophage strain specific against bacteria belonging to the genus *Enterococcus* deposited in the Polish Microorganism Collection as deposit number PCM F/00030.

The next subject of the present invention is the use of the bacteriophage strain deposited in the Polish Microorganism Collection as deposit number PCM F/00030 in the production of preparations antibacterial used to combat bacteria belonging to the genus *Enterococcus*. Preferentially, the targeted bacteria belong to the species *Enterococcus faecalis*.

Another subject the present invention is a bacteriophage strain specific against bacteria belonging to the genus *Enterococcus* deposited in the Polish Microorganism Collection as deposit number PCM F/00031.

The next subject the present invention is the use of the bacteriophage strain deposited in the Polish Microorganism Collection as deposit number PCM F/00031 in the production of preparations antibacterial used to combat bacteria belonging to the genus *Enterococcus*. Preferentially, the targeted bacteria belong to the species *Enterococcus faecalis*.

Another subject the present invention is a bacteriophage strain specific against bacteria belonging to the genus *Enterococcus* deposited in the Polish Microorganism Collection as deposit number PCM F/00032.

The next subject of the present invention is the use of the bacteriophage strain deposited in the Polish Microorganism Collection as deposit number PCM F/00032 in the production of preparations antibacterial used to combat bacteria belonging to the genus *Enterococcus*. Preferentially, the targeted bacteria belong to the species *Enterococcus faecalis*.

Another subject the present invention is a bacteriophage strain specific against bacteria belonging to the genus *Enterococcus* deposited in the Polish Microorganism Collection as deposit number PCM F/00033.

The next subject the present invention is the use of the bacteriophage strain deposited in the Polish Microorganism Collection as deposit number PCM F/00033 in the production of preparations antibacterial used to combat bacteria belonging to the genus *Enterococcus*. Preferentially, the targeted bacteria belong to the species *Enterococcus faecalis*.

Another subject the present invention is a bacteriophage strain specific against bacteria belonging to the genus *Enterococcus* deposited in the Polish Microorganism Collection as deposit number PCM F/00034.

The next subject the present invention is the use of the bacteriophage strain deposited in the Polish Microorganism Collection as deposit number PCM F/00034 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00035.

The next subject the present invention is the use of the bacteriophage strain deposited in the Polish Microorganism Collection as deposit number PCM F/00035 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00036.

The next subject the present invention is the use of the bacteriophage strain deposited in the Polish Microorganism Collection as deposit number PCM F/00036 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00037.

The next subject the present invention is the use of the bacteriophage strain deposited in the Polish Microorganism Collection as deposit number PCM F/00037 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00038.

The next subject the present invention is the use of the bacteriophage strain deposited in the Polish Microorganism Collection as deposit number PCM F/00038 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00039.

The next subject the present invention is the use of the bacteriophage strain deposited in the Polish Microorganism Collection as deposit number PCM F/00039 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00040

The next subject the present invention is the use of the bacteriophage strain deposited in the Polish Microorganism Collection as deposit number PCM F/00040 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00041

The next subject the present invention is the use of the bacteriophage strain deposited in the Polish Microorganism Collection as deposit number PCM F/00041 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00042

The next subject the present invention is the use of the bacteriophage strain deposited in the Polish Microorganism Collection as deposit number PCM F/00042 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00043

The next subject the present invention is the use of the bacteriophage strain deposited in the Polish Microorganism Collection as deposit number PCM F/00043 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00044

The next subject the present invention is the use of the bacteriophage strain deposited in the Polish Microorganism Collection as deposit number PCM F/00044 in the production of preparations antibacterial used to combat bacteria belonging to the genus *Enterococcus*. Preferentially, the targeted bacteria belong to the species *Enterococcus faecalis*.

The subject the present invention is a bacteriophage strain specific against bacteria belonging to the genus *Enterococcus* deposited in the Polish Microorganism Collection as deposit number PCM F/00045

The next subject the present invention is the use of the bacteriophage strain deposited in the Polish Microorganism Collection as deposit number PCM F/00045 in the production of preparations antibacterial used to combat bacteria belonging to the genus Enterococcus. Preferentially, the targeted bacteria belong to the species Enterococcus faecalis.

EXAMPLE 1

Phage *Enterococcus faecalis* 1/339/K22228

A virulent bacteriophage isolated from raw sewage at the River Port in Wrocław from the strain *E. faecalis* K 22228.

The phage was isolated after incubation for 1 h at 37° C. of the examined sewage sample in a liquid medium/at a ratio of 1:1/with the addition of 0.1 ml of a fresh culture of strain K 22228. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh K22228 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 74 strains of *E. faecalis*. Weak positive lytic reactions were demonstrated for 3 out of 30 strains of *E. faecium* used in the reaction.

Phage strain *Enterococcus faecalis* 1/339/K22228 was deposited on Jun. 25, 2007 in the w Polish Microorganism Collection in Wrocław, which possesses an international deposit agency status for patent proceedings (IDA). The patent deposit was given the number F/00029.

EXAMPLE 2

Phage *Enterococcus faecalis* 4/R26519

A virulent bacteriophage isolated from the sewage from the Strachocin II treatment plant in Wrocław from the strain *E. faecalis* 26519.

The phage was isolated after incubation for 1 h at 37° C. of the examined sewage sample in a liquid medium/at a ratio of 1:1/with the addition of 0.1 ml of a fresh culture of strain R 26519. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh R 26519 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 65 strains of i E. faecalis.

No positive lytic reactions were demonstrated for 30 strains of *E. faecium* used in the reaction.

Phage strain *Enterococcus faecalis* 1/339/R26519 was deposited on Jun. 25, 2007 in the w Polish Microorganism Collection in Wrocław, which possesses an international deposit agency status for patent proceedings (IDA). The patent deposit was given the number F/00030.

EXAMPLE 3

Phage *Enterococcus faecalis* 1/339/SI22247

A virulent bacteriophage isolated from raw sewage from the River Port in Wrocław from the strain *E. faecalis* 22247.

The phage was isolated after incubation for 1 h at 37° C. of the examined sewage sample in a liquid medium/at a ratio of 1:1/with the addition of 0.1 ml of a fresh culture of strain SI22247. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh SI22247 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 102 strains of *E. faecalis*. Weak positive lytic reactions were demonstrated for 1 out of 30 strains of *E. faecium* used in the reaction.

Phage strain *Enterococcus faecalis* 1/339/SI22247 was deposited on Jun. 25, 2007 in the w Polish Microorganism Collection in Wrocław, which possesses an international deposit agency status for patent proceedings (IDA). The patent deposit was given the number F/00031.

EXAMPLE 4

Phage *Enterococcus faecalis* 1/339/SII 22248

A virulent bacteriophage isolated from raw sewage from the River Port in Wrocław from the strain *E. faecalis* 22248.

The phage was isolated after incubation for 1 h at 37° C. of the examined sewage sample in a liquid medium/at a ratio of 1:1/with the addition of 0.1 ml of a fresh culture of strain SII22248. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh SII22248 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 111 strains of *E. faecalis*. Weak positive lytic reactions were demonstrated for 1 out of 30 strains of *E. faecium* used in the reaction.

Phage strain *Enterococcus faecalis* 1/339/SII22248 was deposited on Jun. 25, 2007 in the w Polish Microorganism Collection in Wrocław, which possesses an international deposit agency status for patent proceedings (IDA). The patent deposit was given the number F/00032.

EXAMPLE 5

Phage *Enterococcus faecalis* and/C22782

A virulent bacteriophage isolated from raw sewage from the River Port in Wrocław from the strain *E. faecalis* C22782.

The phage was isolated after incubation for 1 h at 37° C. of the examined sewage sample in a liquid medium/at a ratio of 1:1/with the addition of 0.1 ml of a fresh culture of strain C22782. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh C22782 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 94 strains of *E. faecalis*. Positive lytic reactions were demonstrated for 2 out of 30 strains of *E. faecium* used in the reaction.

Phage strain *Enterococcus faecalis* 1/339/C22782 was deposited on Jun. 25, 2007 in the w Polish Microorganism Collection in Wrocł aw, which possesses an international deposit agency status for patent proceedings (IDA). The patent deposit was given the number F/00033.

EXAMPLE 6

Phage *Enterococcus faecalis* 2/51c

A virulent bacteriophage isolated from raw sewage from the River Port in Wrocł aw from the strain *E. faecalis* 51c.

The phage was isolated after incubation for 1 h at 37° C. of the examined sewage sample in a liquid medium/at a ratio of 1:1/with the addition of 0.1 ml of a fresh culture of strain 51c. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh 51c culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 102 strains of *E. faecalis*. No positive lytic reactions were demonstrated any of 30 strains of *E. faecium* used in the reaction.

Phage strain *Enterococcus faecalis* 1/339/51c was deposited on Jun. 25, 2007 in the w Polish Microorganism Collection in Wrocł aw, which possesses an international deposit agency status for patent proceedings (IDA). The patent deposit was given the number F/00034.

EXAMPLE 7

Phage *Enterococcus faecalis* 3/J 26271

A mild strain of bacteriophage isolated from strain *E. faecalis* J26271.

The strain was cultured for 18 h at 37° C. After centrifugation for 30 at 4.5 KRPM, the supernatant was filtered through antibacterial filters, and the presence of the phage was checked on selective agar medium on dishes, and the lytic activity of the resulting preparation was assayed.

The isolated bacteriophage was used to determine the lytic activity spectrum using 220 antibiotic resistant strains of *E. faecalis* isolated from patients with prostate and urinary and genital tract infections. Positive lytic reactions were observed for 105 strains of *E. faecalis*. No positive lytic reactions were demonstrated any of 30 strains of *E. faecium* used in the reaction.

Phage strain *Enterococcus faecalis* 3/J 26271 was deposited on Jun. 25, 2007 in the w Polish Microorganism Collection in Wrocł aw, which possesses an international deposit agency status for patent proceedings (IDA). The patent deposit was given the number F/00035.

EXAMPLE 8

Phage *Enterococcus faecalis* 5/V26556

A virulent, multivalent phage preparation composed of isolated phages 1/339/K22228, 4/R26519, 1/339/SI22247, 1/339/SII22248, I/C22782, 2/51c using strain *E. faecalis* V26556. The bacteriophages were replicated using standard methods and combined in equal volumes.

The preparation was used to determine the lytic activity spectrum using 220 antibiotic resistant strains of *E. faecalis* isolated from patients with prostate and urinary and genital tract infections.

Positive lytic reactions were observed for 141 strains of *E. faecalis*.

No positive lytic reactions were demonstrated any of 30 strains of *E. faecium* used in the reaction.

Phage strain *Enterococcus faecalis* 5/V26556 was deposited on Jun. 25, 2007 in the w Polish Microorganism Collection in Wrocł aw, which possesses an international deposit agency status for patent proceedings (IDA). The patent deposit was given the number F/00036.

EXAMPLE 9

Phage *Enterococcus faecalis* 6/M26588

A virulent bacteriophage isolated from raw sewage from the Strachocin II treatment plant in Wrocł aw from the strain *E. faecalis* 26588.

The phage was isolated after incubation for 1 h at 37° C. of the examined sewage sample in a liquid medium/at a ratio of 1:1/with the addition of 0.1 ml of a fresh culture of strain R 26588. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh M26588 culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections.

Positive lytic reactions were observed for 95 strains of *E. faecalis*.

No positive lytic reactions were demonstrated for 30 strains of *E. faecium* used in the reaction.

Phage strain *Enterococcus faecalis* 6/M26588 was deposited on Jun. 25, 2007 in the w Polish Microorganism Collection in Wrocł aw, which possesses an international deposit

EXAMPLE 10

Phage *Enterococcus faecalis* 7/P26589

A virulent bacteriophage isolated from raw sewage from the Strachocin II treatment plant in Wrocław from the strain *E. faecalis* 26589.

The phage was isolated after incubation for 1 h at 37° C. of the examined sewage sample in a liquid medium/at a ratio of 1:1/with the addition of 0.1 ml of a fresh culture of strain P26589. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh P26589. culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 95 strains of *E. faecalis*. A positive lytic reaction was demonstrated for 1 of the 30 strains of *E. faecium* used in the reaction.

Phage strain *Enterococcus faecalis* 6/P26589. was deposited on Jun. 25, 2007 in the w Polish Microorganism Collection in Wrocław, which possesses an international deposit agency status for patent proceedings (IDA). The patent deposit was given the number F/00038.

EXAMPLE 11

Phage *Enterococcus faecalis* 8/V26344

A virulent bacteriophage isolated from raw sewage from the Strachocin II treatment plant in Wrocław from the strain *E. faecalis* V26344.

The phage was isolated after incubation for 1 h at 37° C. of the examined sewage sample in a liquid medium/at a ratio of 1:1/with the addition of 0.1 ml of a fresh culture of strain V26344. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh V26344. culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 91 strains of *E. faecalis*. No positive lytic reaction was demonstrated for any of the 30 strains of *E. faecium* used in the reaction.

Phage strain *Enterococcus faecalis* 8/V26344. was deposited on Jun. 25, 2007 in the w Polish Microorganism Collection in Wrocław, which possesses an international deposit agency status for patent proceedings (IDA). The patent deposit was given the number F/00039.

EXAMPLE 12

Phage *Enterococcus faecalis* 9/V26344

A mild strain of bacteriophage isolated from strain *E. faecalis* V26344.

The strain was cultured for 18 h at 37° C. After centrifugation for 30 at 4.5 KRPM, the supernatant was filtered through antibacterial filters, and the presence of the phage was checked on selective agar medium on dishes, and the lytic activity of the resulting preparation was assayed.

The isolated bacteriophage was used to determine the lytic activity spectrum using 220 antibiotic resistant strains of *E. faecalis* isolated from patients with prostate and urinary and genital tract infections. Positive lytic reactions were observed for 113 strains of *E. faecalis*. No positive lytic reactions were demonstrated in any of the 30 strains of *E. faecium* used in the reaction.

Phage strain *Enterococcus faecalis* 9/V26344 was deposited on Jun. 25, 2007 in the w Polish Microorganism Collection in Wrocław, which possesses an international deposit agency status for patent proceedings (IDA). The patent deposit was given the number F/00040.

EXAMPLE 13

Phage *Enterococcus faecalis* 10/R26636

A mild strain of bacteriophage isolated from strain *E. faecalis* R26636.

The strain was cultured for 18 h at 37° C. After centrifugation for 30 at 4.5 KRPM, the supernatant was filtered through antibacterial filters, and the presence of the phage was checked on selective agar medium on dishes, and the lytic activity of the resulting preparation was assayed.

The isolated bacteriophage was used to determine the lytic activity spectrum using 220 antibiotic resistant strains of *E. faecalis* isolated from patients with prostate and urinary and genital tract infections. Positive lytic reactions were observed for 125 strains of *E. faecalis*. A positive lytic reaction was demonstrated for the isolated phage in 1 of the 30 strains of *E. faecium* used in the reaction.

Phage strain *Enterococcus faecalis* 10/R26636 was deposited on Jun. 25, 2007 in the w Polish Microorganism Collection in Wrocław, which possesses an international deposit agency status for patent proceedings (IDA). The patent deposit was given the number F/00041.

EXAMPLE 14

Phage *Enterococcus faecalis* 11/C22782

A mild strain of bacteriophage isolated from strain *E. faecalis* C22782.

The strain was cultured for 18 h at 37° C. After centrifugation for 30 at 4.5 KRPM, the supernatant was filtered through antibacterial filters, and the presence of the phage was checked on selective agar medium on dishes, and the lytic activity of the resulting preparation was assayed.

The isolated bacteriophage was used to determine the lytic activity spectrum using 220 antibiotic resistant strains of *E. faecalis* isolated from patients with prostate and urinary and genital tract infections. Positive lytic reactions were observed for 143 strains of *E. faecalis*. No positive lytic reaction was demonstrated for the isolated phage in any of the 30 strains of *E. faecium* used in the reaction.

Phage strain *Enterococcus faecalis* 11/C22782 was deposited on Jun. 25, 2007 in the w Polish Microorganism Collection in Wrocł aw, which possesses an international deposit agency status for patent proceedings (IDA). The patent deposit was given the number F/00042.

EXAMPLE 15

Phage *Enterococcus faecalis* 12/R26636

A virulent bacteriophage isolated from sewage from the Nieciszów II sewer from the strain *E. faecalis* R26636.

The phage was isolated after incubation for 1 h at 37° C. of the examined sewage sample in a liquid medium/at a ratio of 1:1/with the addition of 0.1 ml of a fresh culture of strain R26636. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh R26636. culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 118 strains of *E. faecalis*. No positive lytic reaction was demonstrated for any of the 30 strains of *E. faecium* used in the reaction.

Phage strain *Enterococcus faecalis* 12/R26636. was deposited on Jun. 25, 2007 in the w Polish Microorganism Collection in Wrocł aw, which possesses an international deposit agency status for patent proceedings (IDA). The patent deposit was given the number F/00043.

EXAMPLE 16

Phage *Enterococcus faecalis* 13/A26696

A virulent bacteriophage isolated from sewage from the Strachocin treatment plant from the strain *E. faecalis* A26696.

The phage was isolated after incubation for 1 h at 37° C. of the examined sewage sample in a liquid medium/at a ratio of 1:1/with the addition of 0.1 ml of a fresh culture of strain A26696. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh A26696. culture and incubated for 18 h w 37° C. The produced phage lysate was centrifuged for 30 min. at 4.5 KRPM and filtered through antibacterial filters, and controlled for the presence of the phage as well.

The isolated bacteriophage was used to determine the lytic activity spectrum using 220 antibiotic resistant strains of *E. faecalis* isolated from patients with prostate and urinary and genital tract infections. Positive lytic reactions were observed for 119 strains of *E. faecalis*. No positive lytic reaction was demonstrated for any of the 30 strains of *E. faecium* used in the reaction.

Phage strain *Enterococcus faecalis* 13/A26696. was deposited on Jun. 25, 2007 in the w Polish Microorganism Collection in Wrocł aw, which possesses an international deposit agency status for patent proceedings (IDA). The patent deposit was given the number F/00044.

EXAMPLE 17

Phage *Enterococcus faecalis* 14/K24274

A virulent bacteriophage isolated from sewage from a raw sewage feeder in irrigated fields of the city of Wrocł aw from the strain *E. faecalis* K24274.

The phage was isolated after incubation for 1 h at 37° C. of the examined sewage sample in a liquid medium/at a ratio of 1:1/with the addition of 0.1 ml of a fresh culture of strain K24274. Next, 0.2 ml of the studied mixture was extracted and smeared on the surface of a dish with a selective agar medium. The dish was incubated for 18 h at 37° C. The phage line was derived from individual colonies using a wire loop. The colonies were transferred into tubes of nutritive broth containing 0.05 ml of a fresh K24274. culture and incubated for 18 h w 37° C. The produced phage lysate was centrifuged for 30 min. at 4.5 KRPM and filtered through antibacterial filters, and controlled for the presence of the phage as well.

Phage strain *Enterococcus faecalis* 14/K24274. was deposited on Jun. 25, 2007 in the w Polish Microorganism Collection in Wrocł aw, which possesses an international deposit agency status for patent proceedings (IDA). The patent deposit was given the number F/00045.

The Polish Microorganism Collection in Wroclaw, i.e., Polish Collection of Microorganisms or PCM, is located at the Institute of Immunology and Experimental Therapy, Polish Academy of Sciences, Il. Weigla 12, 53-114 Wroclaw, Poland.

The invention claimed is:

1. An isolated bacteriophage strain specific against bacteria belonging to the genus *Enterococcus* selected from among the isolated bacteriophage strains deposited in the Polish Microorganism Collection under the deposit numbers: PCM F/00029; PCM F/00030; PCM F/00031; PCM F/00032; PCM F/00033; PCM F/00034; PCM F/00035; PCM F/00036; PCM F/00037; PCM F/00038; PCM F/00039; PCM F/00040; PCM F/00041; PCM 9/00042; PCM 9/00043; PCM 9/00044 or PCM F/00045.

2. The isolated bacteriophage strain of claim 1, wherein the bacteriophage strain is a multivalent bacteriophage strain.

3. An antibacterial preparation comprising the isolated bacteriophage strain of claim 1.

4. An antibacterial preparation comprising the isolated bacteriophage strain of claim 2.

5. The antibacterial preparation of claim 3, wherein the antibacterial preparation is effective against bacteria belonging to the species *Enterococcus faecalis*.

6. The antibacterial preparation of claim 4, wherein the antibacterial preparation is effective against bacteria belonging to the species *Enterococcus faecalis*.

7. A method of treating a bacterial infection, comprising contacting bacteria of the bacterial infection with the antibacterial preparation of claim 3.

8. A method of treating a bacterial infection, comprising contacting bacteria of the bacterial infection with the antibacterial preparation of claim 4.

9. A method of treating a bacterial infection, comprising contacting bacteria of the bacterial infection with the antibacterial preparation of claim 5.

10. A method of treating a bacterial infection, comprising contacting bacteria of the bacterial infection with the antibacterial preparation of claim 6.

* * * * *

UNITED STATES PATENT AND TRADEMARK OFFICE
CERTIFICATE OF CORRECTION

PATENT NO. : 8,440,446 B2  
APPLICATION NO. : 13/059513  
DATED : May 14, 2013  
INVENTOR(S) : Weber-Dabrowska et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 107 days.

Signed and Sealed this

Eighth Day of September, 2015

Michelle K. Lee
*Director of the United States Patent and Trademark Office*